United States Patent
Keller et al.

(12)

(10) Patent No.: US 6,180,106 B1
(45) Date of Patent: Jan. 30, 2001

(54) SYMPTOMATIC RELIEF OF ALLERGIC REACTIONS

(75) Inventors: Robert H Keller, Weston; Xue-Lan Wen, Miami, both of FL (US)

(73) Assignee: Vit-Immune, L.C., Hollywood, FL (US)

( * ) Notice: Under 35 U.S.C. 154(b), the term of this patent shall be extended for 0 days.

(21) Appl. No.: 09/349,100

(22) Filed: Jul. 8, 1999

Related U.S. Application Data

(60) Provisional application No. 60/092,352, filed on Jul. 10, 1998.

(51) Int. Cl.[7] .......................... A01N 65/00; A61K 35/78
(52) U.S. Cl. .......................................... 424/195.1
(58) Field of Search .................. 424/195.1; 514/783

(56) References Cited

U.S. PATENT DOCUMENTS

| | | | |
|---|---|---|---|
| 5,584,140 | * | 12/1996 | Byrne ........................ 47/58 |
| 5,874,084 | * | 2/1999 | Yng-Wong .................. 424/195.1 |

OTHER PUBLICATIONS

Computer JPAB Abstract Yutaka et al JP407048267 Crude–Drug Extract Containing Ginkgo–Leaf Extract and Prunus Mume Immature Fruit Extract And Health Drink Containing The Crude–Drug Extract Feb. 21, 1995.*

Computer JPAB Abstract JP 62096428 Refreshing Drink Containing Plum Component, May 1987.*

Computer Derwent Abstract Gong et al CN 1196954 Compound Gingko Leaf Preparation And Its Prep Method Oct. 28, 1998, Feb. 1995.*

* cited by examiner

*Primary Examiner*—Herbert J. Lilling
(74) *Attorney, Agent, or Firm*—Pitney, Hardin, Kipp & Szuch, LLP

(57) ABSTRACT

The composition disclosed is a unique formulation of Traditional Chinese Medicine (TCM) extracts created to reduce the debilitating symptoms of allergies. It combines a number of organically grown, but, non-organically extracted, standardized formulations of natural ingredients which have been used singly for hundreds of years for symptomatic relief of allergies. These include Ginseng and Gan Cao, which provide a natural anti-inflammatory effect; Bai Gao, which prevent the smooth muscle spasms associated with allergic reactions; Suan Zao ren, which provides an antihistamine effect without the usual sedative effect; and Wu Mai, which reduces the local swelling associated with allergies. Combined, it was unexpectedly found that these ingredients provide a natural, non-drying, non-sedating alternative to antihistamines, without inhibiting the natural healing mechanisms.

14 Claims, 1 Drawing Sheet

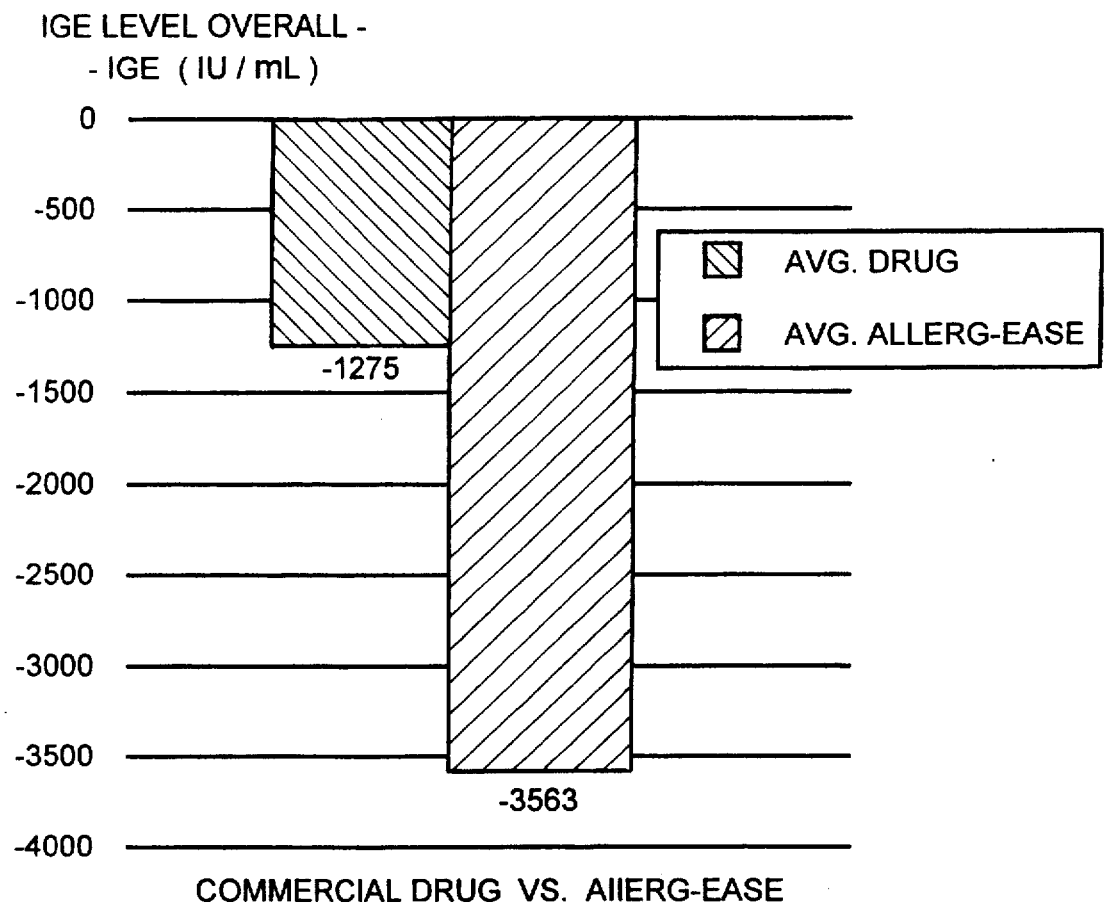

SYMPTOMATIC RELIEF OF ALLERGIC REACTIONS

This application claims priority to U.S. Provisonal Application Ser. No. 60/092,352 filed Jul. 10, 1998.

BACKGROUND OF THE INVENTION

1. Field of the Invention

This invention relates to pharmaceutical compositions and methods for the treatment of mammals suffering symptoms of allergic reactions.

2. Brief Description of Related Art

An allergy is defined as an immune response in a mammal induced by an environmental antigen that has deleterious effects resulting in significant tissue damage and inflammation. Allergies comprise one of the most common medical problems in the twentieth century with some estimates suggesting that as many at 10% of the population may be affected. The antigen (allergen) is a non-parasitic antigen and the immune response is generally a type I hypersensitivity reaction. This reaction, which comprises mast cell or basophil degranulation manifests itself clinically in disorders related to biological effects of mediators released by the degranulation. These mediators are pharmacologically active agents that act on local tissues to increase vascular permeability and inflammation. Primary mediators such as histamine, serotonin, protease, prostaglandins SRS-A and similar substances released during degranulation may actually be more detrimental than beneficial to the comfort and well-being of the affected individual. The biological effects are the symptoms of the hypersensitivity reactions.

The classical treatment of type I hypersensitivity reactions has heretofore comprised administration of, for example, antihistamines or a process termed desensitization. Desensitization involves multiple injections and requires frequent visits to a doctor over a long period of time. Antihistamines are, of course, effective to relieve the symptoms associated with the type I hypersensitivity reaction. Antihistamine treatment suffers from problems including drying of the mucous membranes and sedation as well as manifest side effects of depression and drowsiness. In addition, antihistamines can interact with other medicines. Warnings are given to refrain from operating machinery when antihistamines are administered. Both methods are expensive.

Ideally, the treatment of the symptoms associated with allergic hypersensitivity reactions avoids the administration of antihistamines or blocks the other mediators in the allergic cascade causing a reduction in the symptoms.

It has been observed that traditional Chinese pharmacopoeia includes medicinals which have been time-tested for safety and effectiveness. For example, ginseng has been used in China for over 5,000 years. In a traditional Chinese medical context, ginseng is a "tonic" or "adaptogen" considered by many to be a substance which is not harmful and causes minimal changes or symptoms in the physiological functions of an organism. This herbal root is used throughout Asia to promote an overall sense of well being, stamina and strength. In this regard, it is believed by many that ginseng preparations act to modulate stress, replenish vital energy, improve performances under a wide variety of stressful conditions, increase blood volume, promote appetite, quiet the spirit and provide wisdom. It is, in fact, listed in the Merck Index as therapeutically an "aromatic bitter".

However, even in traditional Chinese medicine ginseng is not considered a panacea. The general practioner, after determining a diagnosis and before prescribing medication, will map a course of treatment strategy. When he prescribes medication, including ginseng, he will always prescribe the ginseng in combination with some other remedy which, depending on the diagnosis, will operate in the same direction or in the opposite direction to bring the yin and yang into balance, even though the condition under treatment may respond to administration of ginseng alone.

SUMMARY OF THE INVENTION

The invention comprises a composition for oral or local administration to a mammal suffering a type I hypersensitivity reaction to an allergen, for the relief of symptoms associated with the reaction, which comprises; in admixture, particlized ginseng root;

*Ginko biloba* leaf;

Ziziphus seed;

mume fruit; and licorice root.

The invention also comprises a method for the symptomatic relief of a type I hypersensitivity reaction in a mammal, which comprises orally administering to said mammal an effective dose for said relief, of a mixture of ginseng root, *Ginko biloba* leaf, Ziziphus seed, mume fruit and licorice root.

DETAILED DESCRIPTION OF THE PREFERRED EMBODIMENTS OF THE INVENTION

Those skilled in the art will gain an appreciation of the invention from the following discussion of the preferred embodiments of the invention.

Ginseng (called "renshen" in Chinese) is the root of a botanical, found naturally in China and Korea. The best known ginseng on a worldwide basis is Asian ginseng (*Panax ginseng*), which is also widely cultivated in the United States. There are other varieties, such as Siberian ginseng (*Eleutheroccus senticosus*). The root comprises resin, panaxatriol and other substances containing a steroid nucleus, sugar, starch, mucilage, a saponin, volatile oil or triterpenoid glycosides including, in particular, *P. quinquefolium* and *P. pseudoginseng* which are generally considered to be biologically active. Isolation and identification of ginseng saponins is described in Kaku et al., Arzneimittel-Forsch. 25, 343 (1975). Use in oriental medicine as tonic: K. Chimin Wong, Wu Lien-the, History of Chinese Medicine (Shanghai, 2nd ed., 1936) 906 pp. Comprehensive review of morphology, cultivation and uses appears in Baranov, Econ. Bot. 20, 403–406 (1966).

As a therapeutic composition, Ginseng is classified as an aromatic bitter; Merck Index, No. 4256. It has a sweet, aromatic taste which can be referred to as "exotic".

Research suggests to some that ginseng has nonspecific immunostimulatory activity similar to that of the herb Echinacea.

The present invention does not make any claim for curative benefit from the use of ginseng, but suggests that its inclusion in the composition of the invention has accepted advantages, including but not limited to at least some of the advantages mentioned above.

Dried ginseng root is generally administered to adults in doses of 2 to 8 grams per day (when used singly).

The leaf of the *Ginkgo biloba* tree is rich in flavonoid glycosides content along with ginkogolides and bilbalides.

Ginkgo biloba is a chemical mediator of allergic symptoms in the group of substances termed leukotrienes. Although these chemicals are partially inhibited by licorice, they are more completely inhibited by Ginkgo. As such, these herbs in combination serve to more effectively block the inflammatory component of allergies by inhibiting the effects of multiple inflammatory mediators. Extracts of the leaf (24% extract) are commercially available from a number of providers (for example, Boehringer Ingelheim Pharmaceuticals, Inc., Ridgefield, Conn.) who manufacture a standardized 24 percent extract. The extract (Chinese name: bai goo) has been identified as a mild sedative which prevents smooth muscle spasms associated with type I hypersensitivity reactions. The herb is also a stimulant to the circulatory system. The dosage administered to adults is generally within the range of 40 to 120 mg/per day (when used singly).

The seed of Ziziphus jujuba (Rhamnaceae) known in China as suan zao ren provides an antihistamine effect without the usual sedative side effect. This herb acts as a general calmer to the immune system without compromising its ability to defend us from bacteria, viruses etc. Suan zao ren functions in allergic reactions to decrease the levels of symptoms by decreasing immune chemicals. In addition, it contains Vitamin C which also has been shown to be protective in allergic conditions. It may be administered to adults in a dosage of from 6 to 15 gms/day (used singly). The Chinese use this medication to calm the nerves and relax the body.

Commonly called licorice root, the root of Glycyrrhiza uralensis (leguminosae) known also as "gan cao" or Chinese licorice is used in Chinese medicine to slow and prolong the effect of strong tonics. In combination with the ginseng it functions to provide a prolonged anti-inflammatory effect. It is generally administered to adults in a dosage of 2 to 10 grams/day (when used singly). Equivalent sources of glycyrrhiza are the root of G. glabra L. variety typica (Spanish licorice) and other varieties containing 6–14 percent of glycyrrhizn (the glucoside of glycyrrhetic acid). Inflammation is a central phenomenon associated with all allergic reactions and the reason that allergic symptoms are frequently treated with local steroids as well as antihistamines. Licorice provides a natural alternative and in conjunction with Ginseng provides both a significant anti-inflammatory as well as an antihistamine effect. In addition, it provides a natural suppressant for the coughs that commonly accompany allergic reactions.

The unripened, dried fruit of the tree Prunus mume known as "black-plums" and known in China wu mei, is possessive of astringent properties. This traditional Chinese herb has a variety of effects. In the context of allergies, however, it has both a direct antihistaminic effect as well as preventing the vascular leakiness associated with sever allergies. The mechanism by which this occurs remains obscure. When used in the present invention at a dosage of 100 to 600 mg per day, the ingredient functions to reduce local swelling, of tissues, associated with the type I hypersensitivity reaction.

The ingredients described above in combination, work synergistically to provide the necessary action required for response to type I hypersensitivity reaction to an allergen, while supporting the mammal's ability to heal itself since administration of the combination does not inhibit natural tissue repair mechanisms. The ingredients work together to calm the biochemical triggers and clinical symptoms of allergies without the expense and inconvenience of desensitization or the sedating and drying effects of antihistamines. This gains importance as allergic symptoms (which result from the release of chemicals from the surface of basophils and mast cells) are caused not only by histamine but by a variety of chemicals. As a result, antihistamines, the most commonly used anti-allergy therapy, cannot totally block symptoms as they do not prevent the actions of other released chemicals.

As each of these ingredients has properties which enhances the properties of the others, it is preferable that there be at least 3% of each of the ingredients in the compound. In more preferred embodiments, there is at least 10% of each of the following ingredients: Ziziphus seed; mume fruit; and licorice root. It will be appreciated that the proportion of the ingredients may be adjusted to address the individual needs of patients depending on the severity of the various symptoms of allergies such as sneezing, coughing, stuffy nose, headaches, nausea, itching, and various other associated symptoms.

Clinical Testing

The efficacy of the compound has been demonstrated in clinical tests. Ten patients were on a treatment of prescription antihistamines (sold under the trademarks Claritin® or Zyrtec®) for a period of 6 to 8 months. Then the patients were taken off the prescription antihistamines and instead given a two dosage units twice a day (as described in Example 1 below) of the inventive compound for a period of 6–9 months.

BRIEF DESCRIPTION OF THE DRAWINGS

FIG. 1 shows a graph which indicates that the IgE level (which is a standard measure of the presence of allergen) in patients taking the inventive compound was significantly reduced (by 3563) after a patient is given Applicant's inventive compound when compared with patients the traditional antihistamine where the reduction was 1275. This demonstrates that the inventive compound is almost three times as effective in reducing allergies as currently prescribed commercial brands.

This invention also relates to pharmaceutical dosage unit forms for systemic administration (oral) which are useful in treating mammals, including humans to relieve the symptoms of a type I allergic reaction. The term "dosage unit form" as used in this specification and in the claims refers to physically discrete units suitable as unitary dosage for mammalian subjects, each unit containing a predetermined quantity of the essential active ingredient; calculated to produce the desired effect in combination with the required pharmaceutical means which adapt said ingredient for systemic administration. Examples of dosage unit forms in accordance with this invention are tablets, capsules, orally administered liquid preparations in liquid vehicles and dry preparations for the extemporaneous preparation of preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate, magnesium stearate and the like. Liquid pharmaceutical preparations for oral administration may be prepared in water or aqueous solutions which advantageously contain suspending agents, such as for example, sodium carboxymethylcellulose, methylcellulose, acacia, polyvinyl pyrrolidone, polyvinyl alcohol and the like. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, water, ethanol, and polyols, for example, glycerol, propylene glycol, liquid polyethylene glycol, and the like.

The pharmaceutical dosage unit forms are prepared in accordance with the preceding general description to provide an effective amount of the essential active ingredient per dosage unit form in admixture with the means for adaptation to systemic administration. In general, the unit dose form will contain 5 to 95 percent by weight of the essential active ingredient.

It is also contemplated that the composition may be applied topically to relieve allergic reactions which manifest itself in the form an itch. Suitable vehicles to act as a pharmaceutically acceptable carriers for topical administration are found in U.S. Pat. Nos. 5,916,905 and 5,902,827 incorporated herein by reference and are known to those skilled in the art.

It will be appreciated that the exact dosage of the essential active ingredient constituting an effective amount for treatment of a mammal according to the method of the invention will vary greatly depending on the specific nature of the clinical condition being treated, severity of the condition, species of mammal; age, weight and condition of the mammal and the specific formulation being administered. The exact dose required for a given situation may be determined by administration of a trial dose and observation of the clinical response. In general, an effective amount to be administered will be within a range of from about 0.1 mg. per kg. to about 50 mg. per kg. of body weight of the recipient, daily. Preferably 0.5 mg./kg. to about 25 mg./kg. daily is provided. In most instances. In cases such as the treatment of hay fever, it may be desirable to repeat the administrations several times daily over periods of time.

The following examples and preparations describe the manner and process of making and using the invention and set forth the best mode contemplated by the inventor of carrying out the invention but are not to be construed as limiting.

EXAMPLE 1

A mixture of the following ingredients is prepared by hand mixing:

| English Name | Chinese Name | Source | Amount |
| --- | --- | --- | --- |
| Ginseng 20% | ren shen | root | 100 mg |
| Ginkgo biloba 24% | bai gao | leaves | 30 mg |
| Ziziphus | suan zao ren | seed | 20 mg |
| Mume Fruit | wu mei | fruit | 100 mg |
| Licorice Root | gan cao | root | 50 mg |

The mixture which constitutes the essential active ingredient of the composition of the invention, may be compounded into wafers, tablets or capsules containing 330 to 500 mg of active ingredient. In an uncompounded form, the mixture may be orally administered to an adult human 1 to 4 times a day or as recommended by a health care professional. Alternatively, the mixture may be mixed with juice, water or food to facilitate oral administration.

EXAMPLE 2

Three thousand tablets for oral use, each containing 330 to 500 mg of essential active ingredient are prepared from the following ingredients:

| | |
| --- | --- |
| essential active ingredient (Example 1) | 1500 g |
| starch (Rx-1500) | 300 g |
| magnesium stearate, USP | 39 g |
| colloidal silicic acid | 19.5 g |
| Avicel® pH 102. q.s. to | 3900 g |

The essential active ingredient is ground through a 0.25 mm sieve opening screen. The powdered active ingredient, with 50% of the total amount of magnesium stearate be used, colloidal silicic acid and Ayicel® pH 10.2 are passed through a 40 mesh sieve, mixed for 20 minutes and then slugged. The slugs are broken down by forcing through a screen No. 11, and mixed with the remaining magnesium stearate and compressed into tablets.

One tablet given orally 1 to 4 times a day is useful in the relief of symptoms of inflammation in adult humans provoked by allergic response, or like etiological causes.

EXAMPLE 3

Three thousand capsules for oral use, each containing 330 to 500 mg of the essential active ingredient, from Example 1, supra., are prepared from the following ingredients:

| | |
| --- | --- |
| essential active ingredient (Example 1) | 330-500 g |
| colloidal silicic acid | 30 g |
| magnesium stearate USP | 30 g |
| microcrystalline cellulose | 150 g |
| lactose | 90 g |

In accordance with the active ingredient potency, the amount of lactose is adjusted to achieve a weight of 900 mg for each capsule. The ingredients are passed through a 40 mesh sieve and mixed for 30 minutes. Hard gelatin capsules No. 0 are filled using Zanazi, model RV-59 equipment. The capsules are preserved in airtight, light-resistant containers. For adults, a suggested use: Take 1 to 2 capsules, two times daily during the allergy season, as a dietary supplement or as directed by a health case practitioner.

What is claimed is:

1. A composition of matter, comprising an admixture of particles of the following ingredients:

gingseng root;

*gingko biloba* leaf;

Ziziphus seed;

mume fruit;

licorice root;

wherein the composition comprises at least about 3% of each of said ingredients.

2. The composition of claim 1 where the composition comprises at least 10% of each of the following ingredients: mume fruit and licorice root.

3. The composition of claim 1 further comprising flavorants.

4. The composition of claim 1 further comprising a liquid or solid pharmaceutically acceptable carrier.

5. The systemic administration of a pharmaceutically effective amount of the composition according to claim 1 or 2 to a mammal suffering a type I hypersensitivity reaction to an allergen, for the relief of symptoms associate with the reaction.

6. The systemic administration of a pharmaceutically effective amount of the composition according to claim 1 to a mammal suffering a type I hypersensitivity reaction to an allergen, for the relief of symptoms associate with the reaction.

7. The systemic administration of a pharmaceutically effective amount of the composition according to claim 2 to a mammal suffering a type I hypersensitivity reaction to an allergen, for the relief of symptoms associate with the reaction.

8. The systemic administration of a pharmaceutically effective amount of the composition according to claim 1 to a mammal to act as a cough suppressant.

9. The systemic administration of a pharmaceutically effective amount of the composition according to claim 1 to a mammal to suppress itching.

10. The topical administration of a pharmaceutically effective amount of the composition with a pharmaceutically acceptable carrier according to claim 1 to a mammal to suppress itching.

11. The systemic administration of a pharmaceutically effective amount of the composition according to claim 1 to a mammal to act as an antihistamine.

12. The systemic administration of a pharmaceutically effective amount of the composition according to claim 1 to a mammal to act as an anti-inflammatory.

13. The systemic administration of a composition according to claim 1 of a dosage of 0.1 mg/kg to about 50 mg/kg of body weight of the mammal, daily.

14. The systemic administration of a composition according to claim 1 of a dosage of 0.5 mg/kg to about 25 mg/kg of body weight of the mammal, daily.

* * * * *